United States Patent [19]
Vanderspurt et al.

[11] Patent Number: 5,939,352
[45] Date of Patent: Aug. 17, 1999

[54] ISOBUTANOL SYNTHESIS CATALYST—(LAW092)

[75] Inventors: Thomas Henry Vanderspurt, Delaware Township, N.J.; Mark Alan Greaney, Upper Black Eddy, Pa.; Daniel Paul Leta, Flemington, N.J.; Russell John Koveal, Baton Rouge, La.; Mark Michael Disko, High Bridge, N.J.; Angela V. Klaus, Highland Park, N.J.; Sutinder K. Behal, Somerville, N.J.; Robert B. Harris, Billings, Mont.

[73] Assignee: Exxon Research and Engineering Company, Florham Park, N.J.

[21] Appl. No.: 09/047,204

[22] Filed: Mar. 24, 1998

Related U.S. Application Data

[62] Division of application No. 08/569,382, Dec. 8, 1995, Pat. No. 5,770,541.

[51] Int. Cl.⁶ .............................. B01J 23/32; B01J 23/40; B01J 23/58; B01J 23/60
[52] U.S. Cl. .................... 502/324; 502/325; 502/328; 502/329; 502/339; 502/343; 502/349
[58] Field of Search .................. 502/324, 325, 502/328, 329, 339, 343, 349

[56] References Cited

U.S. PATENT DOCUMENTS

| | | | |
|---|---|---|---|
| 4,659,742 | 4/1987 | Courty et al. | 502/328 |
| 4,675,306 | 6/1987 | Mazanec et al. | 502/303 |
| 4,780,481 | 10/1988 | Courty et al. | 502/302 |
| 5,302,569 | 4/1994 | Horn et al. | 502/329 |
| 5,559,275 | 9/1996 | Barger | 568/905 |
| 5,692,268 | 12/1997 | Koveal et al. | 502/345 |
| 5,707,920 | 1/1998 | Vanderspurt et al. | 502/324 |
| 5,770,541 | 6/1998 | Vanderspurt et al. | 502/324 |

*Primary Examiner*—Mark L. Bell
*Assistant Examiner*—Patricia L. Hailey
*Attorney, Agent, or Firm*—Linda M. Scuorzo

[57] ABSTRACT

The invention relates to a catalyst for conversion of methanol, ethanol alone or in combination with n-propanol to isobutanol and the process for making and using the catalyst. The catalyst is a noble metal supported on at least a first phase of mixed oxide crystallites containing from about 60 to about 74 atomic % (on a metals basis only) zirconium, from about 21 to about 31 atomic % manganese and from about 5 to about 9 atomic % zinc, and less than about 1 atomic % alkali, a second phase of zirconium-doped hetaerolite particles containing from about 65 to about 69 atomic % manganese, from about 31 to about 35 atomic % zinc, from about 0.5 to about 5 atomic % zirconium, and optionally a trace atomic % of alkali, and a third phase containing from about 29 to about 55 atomic % manganese, from about 13 to about 55 atomic % zinc and from about 13 to about 35 atomic % zirconium. The first phase mixed oxide crystallites have a zirconium oxide-like structure have a particle size of at least about 40 Å to about 100 Å, wherein the second phase particles have a particle size of about 200 Å to greater than about 2000 Å, and the third phase has a particle size of about 1000 Å to greater than 4000 Å.

9 Claims, 2 Drawing Sheets

ISOBUTANOL SYNTHESIS CATALYST—
(LAW092)

This is a division of application Ser. No. 569,382, filed Dec. 8, 1995, now U.S. Pat. No. 5,770,541.

1. Field of the Invention

The present invention relates to novel noble metal loaded MnZnr oxide catalysts for coupling of methanol and ethanol; or, methanol, ethanol and n-propanol to higher alcohols, and for incorporation of ethylene into the higher alcohols.

2. Background of the Invention

Environmental and other concerns have increased the demand for oxygenated fuels components for internal combustion engines. For instance, methyl tert-butyl ether (MTBE), tert-amyl methyl ether (TAME) as well as ethyl tert-butyl ether (ETBE) are some potential high octane oxygenates for gasoline engines. This increases the demand for isobutylene, for MTBE and ETBE production, and 2-methyl butylene for TAME production. These olefins can be derived by dehydrating isobutanol and 2-methyl butanol, respectively.

Catalysts, based on zirconium oxide for the conversion of synthesis gas to the foregoing alcohols, but not for the production of isobutanol from methanol-ethanol mixtures, are disclosed in W. Keim and W. Falter, Catalysis Letters, Vol. 3, pp. 59–64, 1989 and M. Roper, W. Keim and J. Seibring, Federal Republic of Germany Patent Application No. 3,524,317A1. However, it is not always practical to convert synthesis gas directly to these alcohols. Instead it is often desirable to convert a mixture of methanol and ethanol in the presence of synthesis gas to isobutanol and 2-methyl butanol and other similar methyl branched alcohols.

Other catalysts, such as gamma alumina impregnated with an inorganic base promoters such as a basic metal salt and a Group VIII metal, are disclosed for example in U.S. Pat. No. 3,972,952 for the vapor phase conversion of methanol and ethanol to higher linear primary alcohols, for instance, n-butanol and n-propanol but not significant levels of isobutanol and 2-methyl butanol.

U.S. Pat. No. 4,681,868 and U.S. Pat. No. 4,935,538 discloses that copper bismuth mixed metal oxide catalyst promoted with alkali couples n-propanol to $C_6$ aldol products but does not disclose the conversion of methanol/ethanol mixtures to isobutanol and 2-methyl butanol. U.S. Pat. No. 5,095,156 discloses that methanol and higher alcohols are coupled in the presence of magnesia, (MgO), and also discloses losses to methane, e.g., the weight % (wt %) selectivity of the water-free products in Table 7 of the patent shows a selectivity to CO and $CO_2$ ranging from 35.8% to 67.7% and selectivity to methane ranging from 6.9% to 12.6% where methanol conversion ranged from 7.6% to 90.6% and ethanol conversion ranged from 20.4% to 99.1%. Such reactions are also discussed by W. Ueda et al. in Catalysis Letters, Volume 12, pages 97 to 104, 1992, although Ueda gives no information of losses to methane.

SUMMARY OF THE INVENTION

Figure 1:
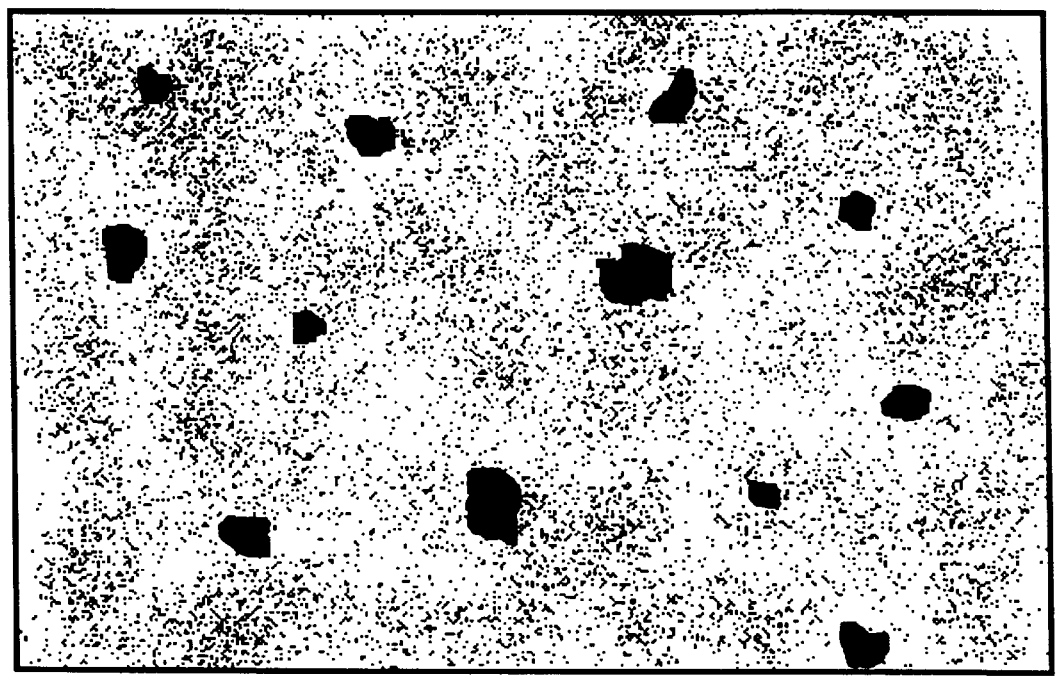
FIG. 1 graphically represents a portion of the protocatalyst before full activation (1.5 cm=0.3 $\mu$m).
Figure 1:
Figure 1:

The present invention provides for a novel noble metal loaded alkali metal doped MnZnZr oxide family of catalysts, their method of preparation and their use in an integrated two stage process for conversion of lower ($C_2$–$C_5$, preferably $C_2$–$C_3$) alcohols and mixtures thereof to isoalcohols, particularly isobutanol. The catalyst also may be used for the conversion of synthesis gas to mixtures of methanol and light alcohols, particularly isobutanol. In one embodiment, the invention provides for a catalyst for conversion of methanol, ethanol alone or in combination with n-propanol to isobutanol and the process for making and using the catalyst.

The catalyst is a noble metal supported on at least a first phase of mixed oxide crystallites containing from about 60 to about 74 atomic % (on a metals only basis) zirconium, from about 21 to 31 atomic % manganese and from about 5 to 9 atomic % zinc, and less than about 1 atomic % alkali, a second phase of zirconium-doped hetaerolite particles containing from about 65 to about 69 atomic % manganese, from about 31 to about 35% zinc, about 0.5 to 5 atomic % zirconium, and optionally a trace atomic % of alkali, and a third phase containing from about 29 to about 55 atomic % manganese, from about 13 to 55 atomic % zinc and from about 13 to 35 atomic % zirconium. The first phase mixed oxide crystallites have a zirconium oxide-like structure having a particle size of about 40 Å to about 100 Å, the second phase particles have a particle size of about 200 Å to greater than about 2000 Å, and the third phase has a particle size of about 1000 Å to greater than 4000 Å.

The invention also provides for a catalyst composition comprising at least a first phase having poorly crystalline manganese and zinc doped zirconium oxide phase containing 71 to 91 atomic % (on a metals only basis) zirconium, 10 to 16 atomic % manganese and 4 to 8 atomic % zinc and a second phase of irregularly shaped hetaerolite-like crystals containing 65 to 69 atomic % manganese, 31 to 35 atomic % zinc and 0 to 5 atomic % zirconium embedded in the first phase.

The invention further comprises a method of making an alkali-doped noble metal loaded mixed manganese, zinc and zirconium oxide isobutanol synthesis catalyst, comprising:

(a) coprecipitating a manganese, zinc and zirconium containing material at essentially constant pH of from 8 to 12 from a solution containing manganese, zinc and zirconium with alkali hydroxides to make the corresponding oxyhydroxide;

(b) washing the precipitate to remove soluble alkali salts;

(c) calcining the precipitate from step (b) in an oxygen containing gas between about 360° C. and about 430° C. to form a mixed metal oxide of the precipitate;

(d) loading the mixed metal oxide of step (c) with a noble metal or a mixture of noble metals;

(e) drying the noble metal loaded mixed metal oxide of step (d);

(f) reducing the material of step (e) in a hydrogen containing gas to produce a highly dispersed noble metal protocatalyst.

In another embodiment, the invention comprises a method for making isobutanol, comprising: contacting a catalyst having a noble metal supported on at least a first phase of mixed oxide crystallites containing from about 60 to about 74 atomic % (on a metals only basis) zirconium, from about 21 to about 31 atomic % manganese and from about 5 to about 9 atomic % zinc, less than about 1 atomic % alkali; a second phase of zirconium doped hetaerolite containing from about 65 to about 69 atomic % manganese, from about 31 to about 35% zinc, from about 1 to about 5 atomic % zirconium, and optionally a trace atomic % of alkali; and a third phase containing from about 29 to about 55 atomic % manganese, from about 13 to about 55 atomic % zinc and from about 13 to about 35 atomic % zirconium, wherein the first phase mixed oxide crystallites have a particle size of about 40 Å to about 100 Å, wherein the second phase particles have a particle size of about 200 Å to greater than 1000 Å, and wherein the third phase has a particle size of about 1000 Å to greater than 4000 Å with a feed containing methanol and a hydrocarbonaceous material selected from the group consisting of ethanol, n-propanol, ethylene and propylene or mixtures thereof and synthesis gas to produce isobutanol.

Also, the invention provides for a method for incorporating a light olefin into alcohol, comprising the steps of contacting a catalyst containing a noble metal supported on at least a first phase of mixed oxide crystallite containing from about 60 to about 74 atomic % (on a metals only basis) zirconium, from about 21 to about 31 atomic % manganese and from about 5 to about 9 atomic % zinc, and less than about 1 atomic % alkali; a second phase of zirconium doped hetaerolite particles containing from about 65 to about 69 atomic % manganese, from about 31 to about 35 atomic % zinc, from about 1 to about 5 atomic % zirconium, and, optionally, a trace atomic % of alkali, and a third phase containing from about 29 to about 55 atomic % manganese, from about 13 to about 55 atomic % zinc and from about 13 to about 35 atomic % zirconium, wherein the first phase mixed oxide crystallites have a particle size of about 40 Å to about 100 Å, wherein the second phase particles have a particle size of about 200 Å to greater than about 2000 Å, wherein the third phase has a particle size of about 1000 Å to greater than about 4000 Å with a reactant stream containing a light olefin selected from the group consisting of ethylene, propylene and mixtures thereof and synthesis gas and optionally methanol to produce a product stream containing the corresponding isoalcohols.

The present invention may suitably comprise, consist or consist essentially of the elements disclosed herein, and may be practiced in the absence of an element or limitation not disclosed as required. The present invention includes the products produced by the processes disclosed herein.

DETAILED DESCRIPTION OF THE INVENTION

Environmental and other concerns have increased the demand for oxygenated fuels components for internal combustion engines. For instance methyl tert-butyl ether (MTBE), tert-amyl methyl ether (TAME) as well as ethyl tert-butyl ether (ETBE) are some potential high octane oxygenates for gasoline engines. This increases the demand for isobutylene for MTBE and ETBE production and 2-methyl butylene for TAME production. These olefins can be derived by dehydrating the corresponding methyl branched alcohols, isobutanol and 2-methyl butanol, respectively. These alcohols in turn can be synthesized by reaction of methanol and ethanol in the presence of synthesis gas and a catalyst. Furthermore, if this reaction is carried out in the presence of synthesis gas and an olefin, such as ethylene, the olefin becomes incorporated into the product isobutanol or 2-methyl butanol and other similar methyl branched alcohols.

The first embodiment of the present invention provides for manganese, zinc, zirconium oxide containing alkali and noble metal containing catalysts. Applicants have found that the composition and microstructure of this catalyst facilitate production of isobutanol from methanol and ethanol or methanol, ethanol and n-propanol. The noble metal is highly dispersed and selected from the group consisting of palladium and platinum, with palladium preferred. Applicants have found that the composition and microstructure facilitate production of isobutanol and methyl butanols.

Although we do not wish to be bound by any specific theory, we believe that the catalyst produces higher alcohols from methanol and ethanol by converting an equilibrium fraction of these feed alcohols to their aldehydes or more likely a surface adsorbed equivalent thereof. These surface species are needed to undergo an "aldol"-like addition. This is the addition of a carbon bearing the aldehydic oxygen to the carbon alpha to another aldehyde group. This results in a molecule that has a carbon bearing an alcohol group separated by one carbon atom from the carbon atoms bearing the aldehyde group. Then, in a key step, these molecules dehydrate to form a transient alpha beta unsaturated aldehyde before being rehydrogenated to the saturated alcohol. When methanol and ethanol are the only feed species besides synthesis gas they first combine to form a surface three carbon species. This differs from a true aldol reaction as it appears that there is an attack of a $C_1$ species on first a $C_2$ species forming a $C_3$ species. This may desorb and escape the catalyst as n-propanol or be attacked by another methanol derived $C_1$ species forming a 4 carbon species that can eventually desorb and escape as isobutanol. While isoalcohols, like isobutanol, might dehydrogenate to the aldehyde and undergo an aldol type addition, they cannot dehydrate since the carbon atom alpha to the carbon bearing the newly formed hydroxyl group is quaternary, that is, it does not bear a hydrogen atom, thus the reaction reverses.

The second embodiment of this invention is a method of preparation of this catalyst via the constant temperature and pH precipitation of a complex mixed metal oxyhydroxide that after calcination, loading with the noble metal and further calcination, forms a first catalyst (protocatalyst). This protocatalyst on exposure to synthesis gas at operating pressure and temperatures undergoes solid state reactions which convert it into an active and selective catalyst. Although the protocatalyst has the same overall global metals composition of the final catalyst, the microstructure of protocatalyst and final catalyst are different. The protocatalyst, upon treatment under synthesis gas between about 360° C. and about 390° C., preferably about 380° C., results in the formation of a catalyst having three phases.

Figure 2:
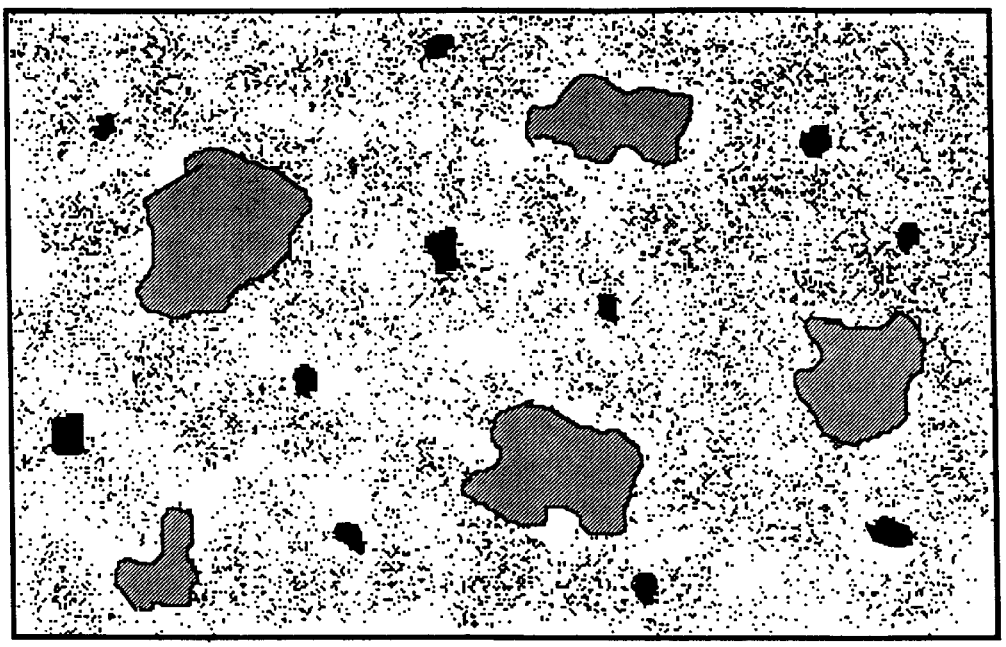
FIG. 2 graphically represents a portion of the activated catalyst after more than 80 hours under synthesis gas at 380° C. (1.5 cm=0.3 $\mu$m).
Figure 2:
Figure 2:
Figure 2:
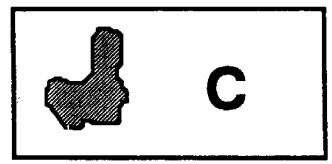

The composition of these catalyst phases is given herein on an atomic percentage basis excluding oxygen and noble metals. The first phase, A' in FIG. 2, which is largest in volume and available surface area, is about 60 to about 74 atomic % (on a metals only basis) zirconium (preferably tetragonal, cubic or mixtures thereof), about 21 to about 31 atomic % manganese, about 5 to about 9 atomic % zinc mixed oxide in the form of about <40 Å to about 100 Å crystallites with a $ZrO_2$-like structure that also contain a minor amount (<1%) of alkali. The noble metal is principally associated with this phase. The noble metal may be in the form of a noble metal, a noble metal-containing alloy or mixed metal clusters. The noble metal is highly dispersed, typically 75% to 100% dispersion. The second phase, B' in FIG. 2, is comprised of larger crystallites (from about 200 Å to about 1000 Å crystallites), with a concomitantly lower surface area. This phase has the composition and structure of a Zr doped hetaerolite where the Mn/Zn ratio is approximately 2 to 1, that is about 65 to about 69 atomic % manganese, about 31 to about 35 atomic % zinc and about 0.5 to about 5 atomic % zirconium in crystallites that may also contain a small amount (0.1 atomic %) of alkali metal. The third phase, C' in FIG. 2, which is present in an active catalyst is zirconium doped manganese-zinc phase with a highly variable Mn-Zn ratio. These are relatively large Mn or Zn rich crystallites with a highly variable composition that can range from about 29 to about 55 atomic % manganese, about 13 to about 55 atomic % zinc and about 13 to about 35 atomic % zirconium and range in size from about approximately 1000 Å to >4000 Å.

While not wishing to be bound by any particular theory, Applicants believe that the overall efficiency of the catalyst in converting methanol with ethanol, n-propanol and light ($C_2$ to $C_3$) olefins to the corresponding higher (iso) alcohols depends primarily on the available surface area of the first phase, and that one of the roles of zinc in this phase is to maintain the noble metal highly dispersed thereon. The presence of the other phases are important insofar as they help stabilize the desired active phase.

The protocatalyst is prepared by coprecipitating at an essentially constant pH of between 8 and 12, preferably between 8.5 and 10 a mixed manganese, zinc, zirconium oxyhydroxide with a base selected from the group of alkali hydroxides consisting of LiOH, NaOH, KOH, RbOH, CsOH and mixtures thereof. Temperatures are from about 0° C. up to about 100° C., with suitable regard given to the freezing and boiling points of the solutions used. Preferably, the temperature is between 50° C. and 90° C., most preferably between 60° C. and 80° C. The concentration, temperature and pH at which the co-precipitation is carried out may be varied within the disclosed ranges to produce the protocatalyst. Any soluble form of the transition metals manganese, zinc and zirconium, that are free of potential catalyst poisons, may be used. Manganese nitrate, zinc nitrate and zirconyl nitrate are the preferred starting materials. Constant effective stirring or blending of the solution is necessary during the precipitation. The precipitated solid is then preferably washed with water to remove the alkali salts and other soluble materials. If the conditions of catalyst usage require it, the solid then may be blended with a suitable binder such as "Cab-O-Sil" or a silica or zirconia sol and extruded or formed in another suitable manner known to those skilled in the art.

Preferably the mole ratio of Zr to the sum of the moles of Mn plus Zr is between about 0.41 and about 0.50, more preferably between 0.425 and 0.49, while the mole ratio of Zn to the sum of the moles of Mn and Zr is preferably between 0.29 and 0.40, more preferably between 0.30 and 0.39.

After an optional drying step, the precipitated solids are calcined, preferably in an oxygen containing gas such as air or oxygen, which is free of typical catalyst poisons, such as sulfur compounds. The solid is calcined at a temperature between about 360° C. and about 440° C. for one to 24 hours, preferably between 360° C. and 425° C. and most preferably between 370° C. and 390° C. After calcination, the solid is then cooled to room temperature and loaded with noble metal. Although the Applicants do not wish to be bound by any particular theory, it is believed that the catalyst is more effective if it does not contain strong acid sites which would result in the conversion of the methanol feed to dimethyl ether rather than to the desired higher alcohols by reaction with the corresponding reactants, e.g., ethanol, n-propanol. Hence, the noble metal compound or compounds used should not contain components which might engender acid sites. Materials such as ammonia or amine complexes of palladium or platinum, typically as the nitrate salts, are preferred. It is especially preferred if the amine complex of the noble metal is an ethanolamine complex. Such may be readily obtained by dissolving the noble metal salt (e.g. palladium nitrate) in water along with sufficient ethanolamine. A sufficient amount of ethanolamine is between about 9 to 36 times the molar amount of noble metal used. After noble metal loading, the material is dried either in air or under vacuum and is ready for activation. Depending on the noble metal precursor used, an optional air calcining step, as well as an optional pre-reduction or pre-reduction and passivation step as well-known by those skilled in the art, may be used.

The protocatalyst, thus obtained by coprecipitation and washing will have at least two phases in addition to the noble metal or any added binder support. The first phase, Phase A in FIG. 1, is a continuous phase containing small and often poorly crystalline particles of a manganese and zinc doped zirconium oxide (preferably tetragonal or cubic or mixtures thereof) phase having about 71 to about 91 atomic % (on a metals only basis) zirconium, about 10 to about 16 atomic % manganese and about 4 to about 8 atomic % zinc and also containing the noble metal and alkali. Embedded in this extensive phase is a second, distinct phase, Phase B in FIG. 1, of zirconium doped hetaerolite ($Mn_2ZnO_4$) or hetaerolite-like crystallites (e.g., crystals that give a electron or x-ray diffraction pattern similar to $Mn_2ZnO_4$) containing about approximately about 65 to about 69 atomic % manganese, about 31 to about 35 atomic % zinc and about 0 to about 5 atomic % zirconium. These hetaerolite phase crystallites range in size from approximately 500 Å to about 2000 Å. A few large (>0.2 micron sized) particles of ZnO, sometimes containing some Mn and alkali metal, are occasionally found in less than optimum preparations that are believed to be indicative of insufficiently rapid mixing and pH control during the precipitation step or non-optimum starting metal ratios.

The overall bulk composition of the protocatalyst or catalyst expressed as atomic ratios of the metallic elements a:Mn b:Zn c:Zr has values of between about 3 to about 5 for a, about 2 to about 3 for b, and about 3 to about 5 for c. On the same atomic ratio scale, the value for the alkali metal coefficient is typically less than 0.1. On this material 0.1 to 5 wt % palladium or about 0.2 to about 10 wt % platinum may be used with 0.2 to 2 wt % preferred and palladium preferred. Higher noble metal concentrations unnecessarily add to the cost of the catalyst without a significant benefit.

On reduction in hydrogen and exposure to synthesis gas at from about 360° C. to 390° C., typically 380° C., the protocatalyst is transformed into an active final catalyst phase (synthesis gas treated catalyst), the composition of which was discussed above. The reduction step is typically carried out in a manner that results in a highly dispersed noble metal phase. A typical reduction sequence would include establishing a flow of dry, poison-free inert gas at low pressure through the bed of the protocatalyst at about at least 30 SCCM/cm$^3$ of catalyst volume and heating the reactor to 100° C. at 8° C./minute or less until 100° C. is achieved and holding for at least 20 seconds per cm$^3$ of catalyst volume. Thereafter, hydrogen is gradually introduced (to minimize catalyst decomposition) into the inert gas until the hydrogen partial pressure is between about 60 and about 80 kPa. The reactor temperature then is increased at about 8° C./minute or less until 200° C. is achieved, at which point the temperature is held for about 20 sec/cm$^3$ of catalyst. The temperature is increased at 4° C./min or less to 260° C. and held while the partial pressure of hydrogen is increased up to about 1 atm. or 100 kPa and the hydrogen flow rate increased to about 300 SCCM/cm$^3$ of catalyst. The catalyst is held under these conditions for at least about 3 min/cm³ of catalyst. This gentle reduction sweeps reaction products from the reactor. The reactor temperature is then increased at a rate of 3° C./minute or less until up to about 380° C. to 400° C. is achieved. The catalyst is typically held at that temperature for at least one hour before the introduction of synthesis gas and the increase in pressure to the operating range. It is often advisable to decrease the temperature to about 350° C. before synthesis gas is introduced to avoid the occurrence of any destructive exotherms. If the temperature is decreased before the introduction of synthesis gas, it may be increased at a controllable rate back to about 380° C. once the synthesis gas is introduced and flowing at operating pressure.

The synthesis gas used may have a hydrogen to carbon monoxide ratio of from about 0.1 to 4.0, preferably 0.4 to 2.5, and most preferably from about 0.5 to about 1.5. The synthesis gas may contain up to 50% or more carbon dioxide with less than 10% preferred. This synthesis gas may also contain light olefins, like ethylene or ethylene and propylene, during operation since the catalyst will incorporate a portion of these olefins into the higher alcohol product, but it is usually advisable to introduce these olefins to the catalyst after the catalyst has been operated under synthesis gas for several hours. Of course, the synthesis gas may also contain inert gases such as nitrogen, argon and relatively unreactive hydrocarbons like methane and ethane, etc.

While the protocatalyst can be used directly after reduction in hydrogen, it tends to be more effective if treated or held under synthesis gas, typically from 24 to 96 hours at between 360° C. and 390° C., preferably 370° C. to 390° C., to allow the transformations (i.e., in microstructure to produce the final catalyst) to occur (see Example 23, Table 6 below).

It is important that the combination of the overall elemental composition and microstructure of the catalysts fall within the requirements described herein. Desirably, the result will be a catalyst having high isobutanol selectivity and productivity at relatively low pressures for this type chemistry (pressure up to about 1500 psig (10,350 kPa)).

The operating pressures and temperatures in the process herein are a function of the methanol, hydrogen and carbon monoxide thermodynamics. If the temperature is too high relative to the synthesis gas pressure, methanol will be decomposed to synthesis gas. If the pressure is too high relative to the hydrogen partial pressure, too little dehydrogenation will occur and the rate of coupling will be slow. The ratio of methanol to ethanol, or methanol to ethanol and n-propanol can vary from 50:1 to 4:1, with a preferred range of 15:1 and 5:1, and a more preferred range of 12:1 and 6:1. If the amount of ethanol, or ethanol and propanol is insufficient, the productivity will be low. If the amount of these higher alcohols is excessive, products such as n-butanol from ethanol-ethanol coupling, and 2-methyl pentanol from n-propanol to n-propanol coupling will become significant. Depending on the $H_2$ and CO partial pressures and their ratio, methanol and ethanol, or methanol, ethanol and n-propanol will be smoothly converted to isobutanol with some methyl butanols at temperatures in the range of about 330° C. to 355° C., and above $H_2$ to CO ratios of about 0.8 to about 1.2, with combined partial pressures of about 5600 kPa to about 6600 kPa.

Conversion by the catalyst is preferably greater than 50%, more preferably greater than 80%, most preferably greater than 90% of ethanol fed, and preferably above 70%, more preferably above 80%, of the n-propanol fed.

Similarly, for olefin incorporation into the liquid products to be effective, the synthesis gas hydrogen to CO ratio should be in the 0.4 to 2.1 range, more preferably below 1.5. Synthesis gas with a higher hydrogen content tends to cause excessive olefin hydrogenation.

Table A below gives the composition of the various phases on a metals mole percent basis.

TABLE A

| Phase | Mn | Zn | Zr |
|---|---|---|---|
| A | 13 ± 3 | 6 ± 2 | 81 ± 10 |
| B | 67 ± 2 | 33 ± 2 | 2.5 ± 2.5 |

Phase A is composed of small, Mn doped crystallites of $ZrO_2$ that are responsible for the majority of the protocatalyst surface area. These crystals also contain a small amount of Zn. Phase B consists of hetaerolite, $Mn_2ZnO_4$, crystallites.

Table B describes the catalyst after treatment for more than 80 hours under synthesis gas at 380° C.

TABLE B

| Phase | Mn | Zn | Zr |
|---|---|---|---|
| A' | 26 ± 5 | 7 ± 2 | 67 ± 7 |
| B' | 67 ± 2 | 33 ± 2 | 2.5 ± 2.5 |
| C' | 42 ± 13 | 34 ± 21 | 24 ± 11* |

*Dense agglomerates of the C' type are all relatively rich in Mn and Zn but exhibit a wide range of Mn to Zn ratios.

Phase A' remains the high surface area phase composed of small (about 40 Å to about 100 Å) Mn-doped $ZrO_2$ that have become enriched in Mn while their Zn content hasn't significantly increased. These small crystallites exhibited a high concentration of stacking faults and other defects consistent with the presence of dopant atoms. The diffraction patterns, obtained from these small crystallites, were broad and poorly formed. They were most consistent with that expected for cubic $ZrO_2$ and differing only by the absence of the 102 reflection at 2.1 Å from the pattern expected of tetragonal $ZrO_2$. Monoclinic $ZrO_2$ can be ruled out since many unique reflections expected for that structure were missing. Phase B' are hetaerolite crystallites as in the protocatalyst but are considerably fewer in number and smaller in size. As their diffraction pattern did not change, they gained little if any Zr during catalyst activation. The third phase, C', are dense crystallites, all relatively rich in Mn and Zn, which exhibit a wide range of Mn to Zn ratios.

EXAMPLE 1

Preparation of Protocatalyst A with Ratio of Mn:Zn:Zr of 0.38:0.26:0.30

The protocatalyst was prepared by the constant pH precipitation of a mix oxyhydroxide of Mn, Zn and Zr by a 2 Molar LiOH solution. The Mn, Zn, Zr solution was prepared by dissolving in 500 ml of distilled water the following amounts of manganese, zinc and zirconyl nitrates that were obtained from Aldrich Chemical Company, Inc. of Milwaukee, Wis. 53233 USA. 0.3 Moles, 43.06 g, $Mn(NO_3)_2 \cdot 6 H_2O$, (F.W. 287.04), 0.2 Moles, 29.70 g, $Zn(NO_3)_2 \cdot 6 H_2O$ (F.W. 297.47) and about 0.4 Moles, 46.25 g, $ZrO(NO_3)_2 \cdot xH_2O$ (F.W. 231.23). The resulting solution was 0.9 Molar in transition metals. This solution was added over the course of 30 minutes, with constant stirring, to 600 ml of water held at 70° C. The pH of this 600 ml was initially adjusted to pH 9.0 with LiOH. Over the course of the addition, the addition rate of the transition metal solution and of 2.0 Molar LiOH was controlled to maintain a pH of 9.0. Five minutes after the addition was complete, the pH was observed to drift down to about pH 7 and additional 2.0 Molar LiOH was added to restore pH 9.0. Stirring was continued overnight at 70° C., during which time the suspension was concentrated by water evaporation. The precipitate was isolated by filtration. The filtrate had a pH of 6.26. The solids were resuspended in one liter of distilled water and stirred vigorously for 30 minutes, then recovered by filtration. The pH of the filtrate was 7.07. This washing step was repeated and the pH of the final filtrate was 6.20. It was dried overnight at 130° C. The dried material was ground to a fine powder and calcined in air in a tube furnace, the temperature of which was raised from room temperature to 425° C. over the course of two hours, held at 425° C. for two hours, and allowed to cool to room temperature over the course of two hours. 13.79 g of dry material was recovered. 10 g of this material was treated with 10 ml of distilled water in which 0.0616 g of $Pd(NO_3)_2$ was dissolved along with 15 drops of ethanolamine. After thorough mixing, the slurry was dried in a vacuum oven for six hours. The Pd-loaded and dried catalyst was heated in air, with the temperature increased from ambient to 325° C. over the course of one hour. The temperature was held at 325° C. for three hours, then cooled over the course of one hour.

The BET surface area was 74.1 $m^2/g$, and elemental analysis showed mole fractions of the Mn, Zn, Zr and Li to be respectively 0.3841, 0.2592, 0.2954 and 0.0613. The wt % Pd was 0.24%.

The calcined protocatalyst was crushed to a fine powder; a portion of this solid was then compressed under about 880 $kg/cm^2$ pressure using a stainless steel die 2.56 cm in diameter to form wafers which were then crushed and sieved to obtain a granular material that was retained on an 80 mesh sieve after passing through a 60 mesh sieve (that is, particles with an approximate size of about 180 $\mu$m to about 250 $\mu$m in diameter). 3.0 $cm^3$ of this material, 3.9850 g, was mixed with 6 $cm^3$, 7.1860 g, of 40–60 mesh (that is, about 250 $\mu$m to 425 $\mu$m in diameter), crushed, high purity, acid washed and calcined quartz as a diluent. The resulting mixture was charged to a copper-jacketed, copper-lined stainless steel reactor tube (net I.D. 0.41 inch, 1.0414 cm) equipped with a copper-jacketed 0.125 inch (0.3040 cm) outside diameter thermowell. This reactor was attached to a flow system by means of "VCR" fittings. The catalyst bed was flushed with high purity argon, and then 240 SCCM high purity hydrogen and 180 SCCM high purity argon under an exit pressure of 300 kPa were passed through the catalyst bed as it was heated to 240° C. over the course of 120 minutes. After a one minute hold at 240° C., the argon was turned off and the hydrogen flow rate was increased to 1200 SCCM. The catalyst bed was then heated to 260° C. at 8° C./min and held there for five minutes, then heated at 2° C./min. to 400° C. and held there for one hour, after which time the reactor was cooled to 350° C. at 8° C./minute and held at 350° C. while gas composition was changed to synthesis gas and the system pressurized to about 6540 kPa at the outlet of the catalyst bed. Once synthesis gas flow was established, the catalyst bed could then be heated back to 380° C. at 3° C./min without overheating. The synthesis gas mixture used contained 44.0% carbon monoxide, 39.4% hydrogen, 10.0% argon and 6.6% carbon dioxide. It was held at 380° C. for 92 hours before the temperature was decreased to 360° C. and at 360° C. for an additional 20 hours before the temperature was decreased to 340° C. After 16 hours at 380° C., a methanol ethanol water mixture was introduced and vaporized before the catalyst such that the gas composition entering the catalyst bed was approximately 44% CO, 39.4% $H_2$, 6.6% $CO_2$ and 10.0% Ar synthesis gas, into which was vaporized at a rate of 0.8 liquid hourly space velocity a mixture of 90.00 wt % methanol, 9.56 wt % ethanol and 0.44% water. The overall gas hourly space velocity was then about 8500 V/V/hr.

Analytical transmission electron microscopy was used to characterize the composition and structure of phases in protocatalyst A, and in the same after activation, and used as an alcohol coupling catalyst. The composition (Zr, Mn, Zn) was determined for regions as small as 4 nm (40 Å) using a 200 kV accelerating voltage Philips CM20 field-emission transmission electron microscope equipped with energy-dispersive x-ray (EDX) analysis. Catalyst particles were embedded in an epoxy and then microtomed into about 500 Å-thick slices in order to determine the morphologies of the large scale structures (about $\leq 1$ $\mu$m) while simultaneously making it possible to observe individual small Zr-rich and Mn-rich phases. Quantitative EDX analyses were carried out using macroscopic (about 5 $\mu$m) sampling regions of the starting catalyst as standards for determining k-factors that were subsequently used for analysis of smaller regions in starting and treated catalysts. The small probe available in this field-emission instrument (about 2 nm diameter) made it possible to isolate the EDX signal from individual particles as small as 4 nm with efforts taken to minimize contributions from neighboring particles. Noble metals were located in Zr-rich regions using a Philips EM420ST TEM operated at 100 kV using large sampling regions in Zr-rich or Zr-depleted regions and energy-dispersive x-ray analysis.

Protocatalyst A was found by transmission electron microscopy to have at least two phases in addition to palladium metal. The first phase is a continuous phase containing small (about 40 Å to 50 Å) and often poorly crystalline (as evidenced by the broad electron diffraction lines) particles of a manganese and zinc doped zirconium oxide phase containing about 71 to about 91 atomic % (on a metals only basis) zirconium, about 10 to about 16 atomic % manganese and 4 to about 8 atomic % zinc on an metals only basis. On the basis of electron diffraction patterns, the zirconium dioxide is believed to have a cubic structure. Embedded in this extensive zirconium rich phase is a second, distinct phase of irregular hetaerolite ($Mn_2ZnO_4$) or hetaerolite-like crystallites (e.g., crystals that give an electron or x-ray diffraction pattern similar to $Mn_2ZnO_4$) containing approximately about 65 to about 69 atomic % manganese, about 32 to about 35 atomic % zinc and about 0 to about 5 atomic % zirconium. These range in size from about approximately 500 Å to about approximately 2000 Å.

After activation and use the catalyst was found to have three phases in addition to palladium. The continuous, higher surface area, Zr rich phase had gained Mn and some Zn, while the hetaerolite-like crystallites had decreased considerably in size and number and a third phase of variable composition with variable Mn/Zn ratio had appeared. The first phase, which was largest in volume and available surface area, contained on a metals only basis about 60 to about 74 atomic % (on a metals only basis) zirconium, about 21 to about 31 atomic % manganese, about 5 to about 9 atomic % zinc in the form of about 40 Å to about 100 Å crystallites. Compared to the protocatalyst, these are enriched in Mn, while their Zn content was not significantly increased. These small crystallites exhibited a high concentration of stacking faults and other defects consistent with the presence of dopant atoms. The diffraction patterns obtained from these small crystallites were broad and poorly formed. Their diffraction patterns were most consistent with that expected for cubic $ZrO_2$ and differing only by the absence of the 102 reflection at 2.1 Å from the pattern expected of tetragonal $ZrO_2$. Monoclinic $ZrO_2$ can be ruled out since many unique reflections expected for that structure were missing. Embedded in this extensive zirconium rich phase are irregular hetaerolite ($Mn_2ZnO_4$) or hetaerolite-like crystallites (e.g., crystals that give an electron or x-ray diffraction pattern similar to $Mn_2ZnO_4$). These were smaller in size (200 Å to approximately 1000 Å across) and fewer in number than in the protocatalyst and contained approximately the same concentration of manganese, zinc and zirconium as in the protocatalyst, that is, about 65 to about 69 atomic % manganese, about 31 to about 35 atomic % zinc and about 0 to about 5 atomic % zirconium, and gave the same diffraction pattern as in the protocatalyst. A significant increase in Zr would be expected to alter this pattern as the Zr atom is significantly larger in diameter than either Mn or Zn. Also embedded in the continuous Zr rich phase of the active catalyst was a new phase consisting of dense crystallites all relatively rich in Mn and Zn but which exhibit a wide range of Mn to Zn ratios. This latter phase varies in size as well as composition ranging from about approximately 1000 Å to >4000 Å and from about 29 to about 55 atomic % manganese, about 13 to about 55 atomic % zinc and about 13 to about 35 atomic % zirconium. This phase is large enough to be clearly visible with a scanning electron microscope when a backscattered electron detector was used to obtain average atomic number images of the sample.

EXAMPLE 2

Preparation of Protocatalyst B with a Mn:Zn:Zr Ratio of 0.39:0.27:0.34

This example illustrates the preparation and activation of Catalyst B, a catalyst within the preferred scope of this invention. 0.3 moles, 43.06 g, $Mn(NO_3)_2 \cdot 6H_2O$, (F.W. 287.04), 0.2 moles, 29.70 g, $Zn(NO_3)_2 \cdot 6H_2O$ (F.W. 297.47) and about 0.4 moles, 46.25 g, $ZrO(NO_3)_2 \cdot xH_2O$ (F.W. 231.23) were dissolved in 500 ml distilled water to make solution TM. Similarly, 42 g of $LiOH \bullet H_2O$ were dissolved in one liter of distilled water to make a 1 Molar solution of LiOH designated solution B. At a relative rate of 2.7 for solution TM and 1 for solution B, these two solutions were added with rapid stirring to 600 ml of distilled water at 70° C. such that the pH of the resultant slurry was maintained at 9.0±0.2. The resultant light pinkish precipitate was allowed to cool to room temperature (ca 22° C.) and settle overnight. On filtering off the supernatant, which had a pH of 8.59, a light brown solid was recovered. This was washed with three one-liter portions of distilled water. The pH of the filtrate from each washing was respectively 8.32, 8.15 and 7.56.

After drying in a glass container at 130° C. in air for an extended period of time, 36 g of the dry material were calcined to 380° C. in air. 15 g of the calcined material was then palladium loaded as follows: 376 mg of $Pd(NO_3)_2 \cdot xH_2O$ were dissolved in 20 ml of distilled water along with 30 drops of ethanolamine. The solid and the solution were combined and mixed thoroughly and then dried in a vacuum oven for two hours prior to calcining. The dried solid was heated in air over the course of one hour to 380° C., held at 380° C. for one hour, and then cooled to room temperature over the course of one hour.

The resulting material had a surface area of 75.1 $M^2/g$ and the atomic fractions of Mn, Zn, Zr and Li were respectively 0.3857, 0.2706, 0.3428 and 0.0010.

The material had a Pd concentration of 1.21 wt %. A portion of this solid was then compressed using a stainless steel die to form a wafer which was then crushed and sieved to obtain a granular material that was retained on an 80 mesh sieve after passing through a 60 mesh sieve, that is the granules had a size range of about 180 μm to about 250 μm. 3.0 $cm^3$ of this material, 3.3952 g, were mixed with 6 $cm^3$, 8.0937 g, of 40–50 mesh crushed high purity, acid washed and calcined quartz as a diluent, that is, the irregular quartz chunks were from about 300 μm to 425 μm in diameter. The resulting mixture of catalyst and quartz granules was charged to a copper-jacketed, copper-lined stainless steel reactor tube (net I.D. 0.41 inch, 1.0414 cm), equipped with a copper-jacketed 0.125 inch (0.3040 cm) outside diameter thermowell. This reactor was attached to a flow system by means of "VCR" fittings. The catalyst bed was flushed with high purity argon, and then 240 SCCM high purity hydrogen and 180 SCCM high purity argon under an exit pressure of 300 kPa were passed through the catalyst bed as it was heated to 200° C. over the course of 15 minutes. After a one minute hold at 200° C., the catalyst bed was heated at 40° C./min to 260° C. During a one minute hold at 260° C., the argon was turned off and the hydrogen flow rate was increased to 1200 SCCM. Under this condition, the reactor bed temperature was increased at 3° C./min to 377° C. without overheating. After 60 minutes at 377° C., the temperature was decreased to 350° C. and the gas composition changed to a carbon monoxide, hydrogen, argon, carbon dioxide, blend flowing at about 400 SCCM through the catalyst bed and the reactor pressure was slowly increased to 6500 kPa. The synthesis gas mixture used contained 44.0% carbon monoxide, 39.4% hydrogen, 10.0% argon and 6.6% carbon dioxide. Once this gas mixture was flowing through the system and the reactor pressure was stabilized at about 6550 kPa, the reactor temperature was increased to 377° C. Under these conditions the temperature at the exit of the catalyst bed was about 380° C. The resultant liquid produced from the synthesis gas was about 29.4% water, 67.3% identified organic compounds: methanol, methyl formate, ethanol, n-propanol, isobutanol, n-butanol, 3-methyl 2-butanol, 3-pentanol, 3-methyl-1-butanol, 2-methyl-1-butanol, 4-methyl pentanol, n-pentanol, 2,2-dimethyl 3-pentanone, 2-methyl-1-pentanol, and 2,4 dimethyl-3-pentanol and about 3.3% trace, unidentified organic compounds. The identified organics were 73.6% methanol, 19.6% isobutanol, 1.8% n-propanol, 1.3% methyl butanols and 3.7% other materials on a carbon basis.

EXAMPLE 3

This example illustrates the performance of Catalyst B with a methanol, ethanol, water feed.

After the gas composition of Example 9 (at 380° C.) was changed to 47.1% carbon monoxide, 42.2% hydrogen and 10.7% argon, a 90 wt % methanol, 9.56% ethanol and 0.44% water vapor was added to the gas mixture and fed to the catalyst. Under these conditions, 99.7% of the ethanol was converted to $C_3+$ products through reaction with the methanol. Some methanol was also decomposed into hydrogen and carbon monoxide. In this case, the liquid produced was 11.4% water, 87.4% identifiable organic compounds: methanol, methyl formate, ethanol, n-propanol, isobutanol, n-butanol, 3-methyl-2-butanol, 3-pentanol, 3-methyl-1-butanol, 2-methyl- 1-butanol, 4-methyl-pentanol, n-pentanol, 2,2-dimethyl-3-pentanone, 2-methyl-1-pentanol, and 2,4-dimethyl-3-pentanol and 1.2% trace materials. On a carbon basis, the produced liquid was 45.9% isobutanol, 35% methanol, 4.4% methyl butanols, 4.4% n-propanol, 1.7% 2-methyl-1-pentanol with about 0.13% ethanol and 7.8% miscellaneous organic compounds.

EXAMPLE 4

This example illustrates that Catalyst B, a catalyst within the preferred scope of this invention, is effective in converting a methanol, ethanol, water and n-propanol feed in the essential absence of undesirable hydrocarbons.

The reactor temperature in Example 3 was decreased from about 380° C. to about 340° C. and the liquid feed composition was changed to resemble the liquid produced without the methanol-ethanol vapor feed. Under these conditions, little, if any, methanol was decomposed into gas, and less than 0.1% of the carbon passing through the reactor was converted to hydrocarbon gas. The liquid composition was changed to about 87.2 wt % methanol, 7% ethanol and 5.8% n-propanol. Under these conditions, the ethanol conversion was 90.2% and the n-propanol conversion was 74.9%. The resultant liquid product contained 86.3% identified organic products: methanol, methyl formate, ethanol, n-propanol, isobutanol, n-butanol, 3-methyl-2-butanol, 3-pentanol, 3-methyl-1-butanol, 2-methyl-1-butanol, 4-methyl-pentanol, n-pentanol, 2,2-dimethyl-3-pentanone, 2-methyl-1-pentanol, and 2,4-dimethyl-3-pentanol, 8.9% unidentified organic products and 4.8% water. On a carbon basis, the liquid product contained about 67.7% methanol, 24.4% isobutanol, 2.6% methyl butanols along with 3.5% n-propanol and 1.4% ethanol.

Increasing the temperature of the reactor in Example 4 from 340° C. to 350° C. increased the ethanol conversion to 97.8% and the n-propanol conversion to 88% after over 190 hours on-line. The liquid produced contained on a carbon basis 62.1% methanol, 30.8% isobutanol, 2.1% methyl butanols, along with 0.4% ethanol and 1.9% n-propanol.

EXAMPLE 5

This example illustrates the incorporation of a light olefin, ethylene, into the alcohol product when ethylene is co-fed to the catalyst, along with methanol, ethanol, n-propanol and synthesis gas.

Under the final conditions of Example 4 (350° C. and about 6550 kPa), the feed gas was changed to 44.0% carbon monoxide, 39.4% hydrogen, 10.0% argon and 6.6% polymer grade ethylene. Under these conditions about 25% of the ethylene fed was converted with 80% selectivity to liquids, 19% to ethane and 1% to higher hydrocarbons including n-butane and butenes. The liquid produced on a carbon basis was: 59.3% methanol, 32.4% isobutanol, 2.3% methyl butanols, 2.2% n-propanol, 1% 2-methyl-1-pentanol and 0.4% ethanol along with miscellaneous organic compounds. With an ethylene co-feed, the ethanol conversion was about 97.4% and the n-propanol conversion was about 86.2%. These values were comparable to, or slightly lower than, those without ethylene feed. With ethylene co-fed, the concentration of unidentified organic compounds in the liquid increased from 1.1% to 3.2%. Significantly, ethylene co-feed also increased the productivity of isobutanol by 7.8% and that of methyl butanols by 11%.

EXAMPLE 6

This example illustrates the conversion and disposition of carbon dioxide free synthesis gas and a methanol, ethanol, n-propanol liquid feed over a catalyst within the scope of this invention.

A second 3.0 cm$^3$ (3.1215 g) sample of 60 to 80 mesh (180 $\mu$m to 250 $\mu$m) granules of Protocatalyst B were blended with 6.0 cm$^3$ (6.8880 g) of acid washed and calcined high purity fused quartz crushed and sieved to 40 to 60 mesh (250 $\mu$m to 425 $\mu$m). This mixture was charged into a copper-jacketed, copper-lined stainless steel reactor tube (net I.D. 0.41 inch, 1.0414 cm) equipped with a copper-jacketed 0.125 inch (0.3040 cm) outside diameter thermowell. This reactor was attached to a flow system by means of "VCR" fittings. The catalyst bed was flushed with high purity argon, and then 240 SCCM high purity hydrogen and 180 SCCM high purity argon under an exit pressure of 300 kPa were passed through the catalyst bed as it was heated to 200° C. over the course of 30 minutes. Then, after a one minute hold at 200° C., it was heated to 260° C. over the course of 30 minutes. After one minute at 260° C., the argon was turned off and the hydrogen flow rate was increased to 1200 SCCM. The catalyst bed was then heated to 377° C. over the course of about 50 minutes, then held there for one hour, after which time the reactor was cooled to 350° C. at 2° C./min and held at 350° C. while gas composition was changed to synthesis gas and the system pressurized to about 6540 kPa at the outlet of the catalyst bed. Once synthesis gas flow was established, the catalyst bed could then be heated back to 380° C. in the catalyst bed at 3° C./min without overheating. Once the catalyst reached 380° C. under synthesis gas flowing at 400 SCCM, it was "on-line" and the run time clock was started. The synthesis gas mixture used contained 47.5% carbon monoxide, 42.5% hydrogen and 10.0% argon. After 41 hours on-line, a mixture of 87.41% methanol, 6.42% ethanol, 5.85% n-propanol and 0.32 wt % water was vaporized into the synthesis gas above the catalyst bed at the rate of 2.4 cm$^3$ of liquid at 0° C. per hour. The catalyst bed was held at 380° C. for 64 hours before the temperature was decreased to 350° C.

After 70 hours on-line at a catalyst bed temperature of 350° C. and a feed synthesis gas composition of 47.10 mole % CO, 42.17 mole % H$_2$ and 10.73 mole % Ar as an internal standard, the carbon monoxide conversion was about 1.8%. This was determined using a gas chromatograph that alternately sampled feed and product gas streams. All the gas feeds to the experimental reactor are controlled with electronic mass flow controllers working with a constant feed and back pressure. Thus the flow of the individual gases and of the mixed gas feed to the reactor is effectively constant. Thus, the Molar ratio of carbon monoxide to argon in the feed and product should be constant in the absence of reaction. If a carbon monoxide-consuming reaction occurs over the catalyst, then the ratio of feed carbon monoxide, CO$_f$, to feed argon Ar$_f$ must equal the ratio of product carbon monoxide, COp, plus carbon monoxide consumed, CO$_C$, to product argon, Ar$_p$, that is:

$$CO_f/Ar_f = (CO_p + CO_C)/Ar_p \text{ or } CO_C = (Ar_p CO_f - Ar_f CO_p)/Ar_f$$

A gas chromatograph was used to alternately sample feed and product gas. The carbon selectivity of this converted gas was found to be about 39.2% to carbon dioxide, 60.8% to hydrocarbon gases and effectively none to liquids using the carbon bookkeeping convention that carbon from converted carbon monoxide is first assigned to the observed net carbon dioxide (excess of CO$_2$ in the exit gas over that fed), then to the observed hydrocarbon gases. The balance of the consumed carbon is then assigned to the liquid product, that is:

Moles of CO converted—(moles CO$_2$ produced+moles carbon as hydrocarbon gases)=moles CO converted to liquid.

The carbon distribution of the hydrocarbon gases was: 28.8 C % ethylene, 24.7 C % propylene, 18.8 C % isobutylene, 12.4 C % methane, 11.8 C % ethane, 2.3 C % propane and 1.2 C % isobutane. This composition suggests that most of these gases, with the exception of the methane, arose from the dehydration of the alcohols fed (or produced), forming olefins, with the subsequent hydrogenation of some of these olefins to form paraffins. These data also show that the losses to methane are on the order of 0.2% of the carbon passing through the reactor. The liquid product produced at the same time as above the gaseous products (that is, the liquid collected between 68.5 and 71 hours on-line) contained about 7 wt % water and 93 wt % organic products, of which 99% were identifiable. The breakdown of these organic products on a carbon percent basis is as follows: 62.41 C % methanol, 30.23 C % isobutanol, 2.08 C % n-propanol, 1.96 C % methyl butanols, 0.90 C % ethanol, 0.88 C % 2-methyl pentanol, 0.09 C % n-butanol and about 1.45 C % miscellaneous organic products. This represents about 95.1% ethanol conversion, 88.7% n-propanol conversion. On a methanol, water free basis, the $C_2+$ liquid products were about 80 wt % isobutanol, 6 wt % n-propanol, 5 wt % methyl butanols, 3.0 wt % ethanol and about 6 wt % other products.

EXAMPLE 7

This example demonstrates the performance of a catalyst within the scope of this invention for the incorporation of a light olefin, ethylene, into the liquid product produced from carbon monoxide and hydrogen.

After 77 hours on-line, the gas composition over the catalyst in Example 6 was changed to 43.7 mole % CO, 39.1 mole % $H_2$, 9.9 mole % Ar and 7.3 mole % polymerization grade ethylene. After 89 hours, the liquid feed was turned off and the behavior of the thoroughly activated, lined-out catalyst under the ethylene containing synthesis gas was monitored by gas chromatography using argon as an internal gas standard as above. Using the carbon bookkeeping convention that ethylene could be converted to only ethane or liquid products and that CO could be converted to $CO_2$, liquids or hydrocarbon gases except ethane and ethylene, the following results were obtained: Under these conditions, 16.2% of the ethylene fed was converted to products. The carbon selectivity to ethane was 72.3 carbon % and the selectivity to liquid products 27.7 carbon %. At the same time, the CO conversion averaged 4.3 mole %. Of this, 92.7% on a carbon basis was converted to liquid products, 2.7 C % to carbon dioxide and the balance, 7.3 C % to hydrocarbon gases (except for ethane and ethylene). The breakdown of the hydrocarbon gases on a carbon % basis was as follows: 31.04 C % n-butane, 27.09 C % methane, 10.84 C % propylene, 9.74 C % isobutylene, 6.79 C % isopentene, 6.25 C % propane, 3.79 C % isopentane, 2.53 C % n-butenes, 1.19 C % n-pentane, and 0.11 C % isobutane, along with about 0.63 C % hexenes and hexanes. The liquid product was about 5% water and 95% organic products by weight. The organic products on a carbon % basis were derived 72.7% from the CO that was converted and 27.3% from the ethylene that was converted. It is believed that the carbon derived from the incorporated ethylene is in the $C_2+$ products, especially in the $C_4+$ products. The composition of the liquid products on a carbon basis was: 90.02 C % methanol, 5.81 C % isobutanol, 0.37 C % methyl-butanols, 0.35 C % n-propanol, 0.18 C % 2 methyl-1-pentanol, 0.08 C % ethanol and 0.07 C % n-butanol, with the balance of the carbon in other miscellaneous oxygen-containing organic products.

EXAMPLE 8

This example further illustrates the incorporation of an olefin, ethylene, into the liquid product derived from synthesis gas and a methanol, ethanol, n-propanol liquid feed.

After 165 hours on-line, the 87.41% methanol, 6.42% ethanol, 5.85% n-propanol and 0.32 wt % water liquid feed was once again vaporized into the synthesis gas (43.7 mole % CO, 39.1 mole % $H_2$, 9.9 mole % Ar and 7.3 mole % polymerization grade ethylene) above the catalyst bed at the rate of 2.4 cm$^3$ of liquid (at 0° C.) per hour.

Under these conditions, 8.1% of the ethylene was converted with a carbon selectivity of 26.2% to ethane and 73.8% to "liquid products" with the same convention for carbon book keeping as above. Similarly, 2.5% of the carbon monoxide fed was consumed, being converted with a carbon selectivity of 72.5% to liquids, 21.4% to carbon dioxide and 6.1% to hydrocarbon gases except for ethane and ethylene. The breakdown of the hydrocarbon gases produced was on a carbon % basis as follows: methane 24.58 C %, propylene 20.79 C %, n-butane 19.63 C %, isobutylene 18.04 C %, propane 6.60 C %, isopentene 4.92 C %, isopentane 2.24 C %, n-butenes 2.07 C %, n-pentane 0.82 C % and isobutane 0.31 C %.

The liquid product was about 4% water and about 96% organic products. 66.2% of the carbon in these products was derived from the feed methanol, 13.6% from the feed ethanol and propanol, 10.6% from the feed ethylene and 9.6% from the feed carbon monoxide. These organic products contained on a carbon % basis: 63.24% methanol, 27.21% isobutanol, 3.96% n-propanol, 1.96% methyl butanols, 1.00% ethanol, 0.83% 2-methyl pentanol and 0.16% n-butanol with about 1.64% miscellaneous products.

EXAMPLE 9

Preparation of Protocatalyst C with a Mn:Zn:Zr Ratio of 0.42:0.29:0.29

In 500 ml of distilled water 21.53 g Mn(NO$_3$)$_2$·6 H$_2$O, 14.85 g Zn(NO$_3$)$_2$·6 H$_2$O(F.W. 297.47) and 23.12 g ZrO(NO$_3$)$_2$·xH$_2$O were dissolved. This solution was added over the course of 30 minutes, with constant stirring, to 600 ml of water held at 70° C. The pH of this 600 ml was initially adjusted to pH 9.0 with LiOH. Over the course of the addition, the addition rate of the transition metal solution and of a 21.0 g/l solution of LiOH was controlled to maintain a pH of 9.0. On addition of the transition metal solution and lithium hydroxide, the precipitate slurry was brown from the outset. Stirring was continued for five hours at 70° C. The suspension was allowed to settle overnight at room temperature without stirring. The precipitate was isolated by filtration, then washed three times by resuspension and stirring in a liter of distilled water for an hour at room temperature, followed by filtering to recover the solids for further resuspension. The washed solids were dried overnight at 130° C. The dried material was ground to a fine powder and calcined in air in a tube furnace, the temperature of which was raised from room temperature to 425° C. over the course of two hours, held at 425° C. for two hours and allowed to cool to room temperature over the course of two hours. 16.35 g of dry material was recovered. 15.0 g of this material were treated with 15 ml of distilled water in which 0.0939 g of Pd(NO$_3$)$_2$·xH$_2$O (assay 39.95 wt % Pd) was dissolved along with 15–20 drops of ethanolamine. After thorough mixing, the slurry was dried in a vacuum oven at 80° C. overnight. The Pd-loaded and dried catalyst was heated in air with the temperature increased from ambient to 325° C. over the course of one hour. The temperature was held at 325° C. for three hours, then cooled over the course of one hour.

The BET surface area was 72.1 m$^2$/g, and elemental analysis showed mole fractions of the Mn, Zn, Zr and Li to be respectively 0.4202, 0.2914, 0.2884 and 0.0613. The wt % Pd was 0.24%.

EXAMPLE 10

Preparation of Protocatalyst D with a Mn:Zn:Zr Ratio of 0.40:0.28:0.32

In 500 ml of distilled water 21.53 g, $Mn(NO_3)_2 \cdot 6 H_2O$, 14.85 g, $Zn(NO_3)_2 \cdot 6 H_2O$ and 23.12 g, $ZrO(NO_3)_2 \cdot xH_2O$ were dissolved. This solution was added over the course of 30 minutes, with constant stirring, to 600 ml of water held at 70° C. The pH of this 600 ml was initially adjusted to pH 9.0 with LiOH. Over the course of the addition, the addition rate of the transition metal solution and of a 21.0 g/500 ml solution of LiOH was controlled to maintain a pH of 9.0. On addition of the transition metal solution and lithium hydroxide, the precipitate slurry was lighter in color than similar precipitations conducted at 70° C. Stirring was continued for five hours at 25° C. The suspension was allowed to settle for about 60 hours at room temperature without stirring. The precipitate was isolated by filtration, then washed three times by resuspension and stirring in a liter of distilled water for an hour at room temperature, followed by filtering to recover the solids for further resuspension. The washed solids were dried overnight at 130° C. The dried material was ground to a fine powder and calcined in air in a tube furnace, the temperature of which was raised from room temperature to 425° C. over the course of two hours, held at 425° C. for two hours, and allowed to cool to room temperature over the course of two hours. 15.25 g of dry material were recovered. 15.0 g of this material were treated with 15 ml of distilled water in which 0.0940 g of $Pd(NO_3)_2 \cdot xH_2O$ (assay 39.95 wt % Pd) was dissolved along with 15–20 drops of ethanolamine. After thorough mixing, the slurry was dried in a vacuum oven at 130° C. for two hours. The Pd-loaded and dried catalyst was heated in air with the temperature increased from ambient to 325° C. over the course of one hour. The temperature was held at 325° C. for three hours; then cooled over the course of one hour.

The BET surface area was 78.8 $m^2/g$, and elemental analysis showed mole fractions of the Mn, Zn and Zr to be respectively 0.4023, 0.2823, and 0.3154. The wt % Pd was 0.25%.

EXAMPLE 11 (COMPARATIVE)

Preparation of Catalyst E with a Mn:Zn:Zr Ratio of 0.54:0.29:0.17

In 500 ml of distilled water 0.10 moles, 28.70 g, $Mn(NO_3)_2 \cdot 6H_2O$, 0.05 moles, 11.56 g, $ZrO(NO_3)_2 \cdot xH_2O$ and 0.05 moles, 14.87 g, $Zn(NO_3)_2 \cdot 6 H_2O$ were dissolved, making a solution that was 0.4 Molar in transition metals. A LiOH solution was prepared by dissolving 21.0 g of LiOH in 500 ml distilled water. The transition metal solution was added over the course of 30 minutes, with constant stirring, to 600 ml of water held at 70° C. The pH of this 600 ml was initially adjusted to pH 9.0 with LiOH. Over the course of the addition, the addition rate of the transition metal solution and of 1.0 Molar LiOH was controlled to maintain a pH of 9.0±1.0. Five minutes after the transition metal solution addition was complete, the pH dropped to about 7.0 and more LiOH solution was added to bring it back up to 9.0. The precipitate was a light tanish brown in color. Stirring was continued overnight at 70° C., during which time the suspension was concentrated by water evaporation. The precipitate was isolated by filtration. The filtrate had a pH of 6.26. The solids were resuspended in one liter of distilled water and stirred vigorously for 30 minutes, then recovered by filtration. The pH of the filtrate was 7.07. This washing step was repeated and the pH of the final filtrate was 6.20. The solid appeared to get darker in color and more difficult to filter as the washing proceeded. The solid was dried overnight at 130° C. and 13.91 g of a black material were recovered. The dried material was ground to a fine powder and calcined in air in a tube furnace, the temperature of which was raised from room temperature to 425° C. over the course of two hours, held at 425° C. for two hours and allowed to cool to room temperature over the course of two hours. 13.79 g of dry material were recovered. 10 g of this material were treated with 10 ml of distilled water in which 0.0616 g of $Pd(NO_3)_2 \cdot xH_2O$ (Johnson Matthey) were dissolved along with 15 drops of ethanolamine. After thorough mixing, the slurry was dried in a vacuum oven for 6 hours. The Pd-loaded and dried catalyst was heated in air with the temperature increased from ambient to 325° C. over the course of one hour. The temperature was held at 325° C. for three hours, then cooled over the course of one hour.

The BET surface area was 59 $m^2/g$, and elemental analysis showed mole fractions of the Mn, Zn, Zr and Li to be respectively 0.5390, 0.2892, 0.1674 and 0.0044. The wt % Pd was 0.24%.

EXAMPLE 12 (COMPARATIVE)

Preparation of Catalyst F with a Mn:Zn:Zr Ratio of 0.27:0.22:0.51

In 500 ml of distilled water 28.42 g $Mn(NO_3)_2 \cdot 6H_2O$, 23.05 g $Zn(NO_3)_2 \cdot 6H_2O$ and 74.79 g $ZrO(NO_3)_2 \cdot xH_2O$ were dissolved. The LiOH solution used to precipitate this was prepared by dissolving 42.0 g of $LiOH \bullet H_2O$ (F.W. 41.96) in a liter of distilled water. The transition metal nitrate solution, added over the course of 30 minutes, with constant stirring, to 600 ml of water held at 70° C. The pH of this 600 ml was initially adjusted to pH 9.0 with LiOH. Over the course of the addition, the addition rate of the transition metal solution and of 1.0 Molar LiOH was controlled to maintain a pH of 9.0. Stirring was continued for five hours at 70° C. The suspension was then allowed to settle and cool overnight. The tan-brown gelatinous precipitate was isolated by filtration. The solid was washed three times by resuspension in one liter of distilled water and 30 minutes of vigorous stirring prior to filtration. The recovered solids were dried overnight at 130° C., leading to the recovery of 45.5 g of material. The dried material was ground to a fine powder and 20.0 g was calcined in air in a tube furnace, the temperature of which was raised from room temperature to 425° C. over the course of two hours, held at 425° C. for two hours and allowed to cool to room temperature over the course of two hours. 13.46 g of cooled, calcined material were recovered. This material was treated with 10 ml of distilled water in which 0.0939 g of $Pd(NO_3)_2$ was dissolved along with 15 drops of ethanolamine. After thorough mixing, the slurry was dried in a vacuum oven at 110° C. for six hours. The dried material was then calcined in air as follows: the temperature was increased from room temperature to 325° C. over the course of an hour, then held at 325° C. for three hours before cooling to room temperature over the course of two hours.

The BET surface area was 112.2 $m^2/g$, and elemental analysis showed mole fractions of the Mn, Zn, Zr and Li to be respectively 0.2663, 0.2184, 0.5116 and 0.0037. The wt % Pd was 0.22%.

EXAMPLE 13 (COMPARATIVE)

Preparation of Catalyst G with a Mn:Zn:Zr Ratio of 0.46:0.29:0.25

In 500 ml of distilled water 21.53 g $Mn(NO_3)_2 \cdot 6H_2O$, 17.94 g $Zn(NO_3)_2 \cdot 6H_2O$ and 21.55 g $ZrO(NO_3)_2 \cdot xH_2O$ were dissolved. This solution was added over the course of 30 minutes, with constant stirring, to 600 ml of water held at 70° C. The pH of this 600 ml was initially adjusted to pH 9.0 with LiOH. Over the course of the addition, the addition rate of the transition metal solution and of 1.0 Molar LiOH was controlled to maintain a pH of 9.0. Stirring was continued for five hours at 70° C. The suspension was then allowed to settle and cool overnight. The pale light gray-brown precipitate was isolated by filtration. The filtrate had a pH of 8.72. The solids were resuspended in one liter of distilled water and stirred vigorously for 30 minutes, then recovered by filtration. The pH of the filtrate was 8.04. This washing step was repeated three times and the pH of the filtrates were 7.58, 7.80 and 8.45, respectively. The recovered solids were dried overnight at 130° C., leading to the recovery of 13.5 g of material. The dried material was ground to a fine powder and calcined in air in a tube furnace, the temperature of which was raised from room temperature to 425° C. over the course of two hours, held at 425° C. for two hours and allowed to cool to room temperature over the course of two hours. The material was treated with 20 ml of distilled water in which 0.0814 g of $Pd(NO_3)_2$ was dissolved along with 15 drops of ethanolamine. After thorough mixing, the slurry was dried in a vacuum oven for six hours. The dried material was then calcined in air as follows: the temperature was increased from room temperature to 325° C. over the course of an hour, then held at 325° C. for three hours before cooling to room temperature over the course of two hours.

The BET surface area was 100 $m^2/g$, and elemental analysis showed mole fractions of the Mn, Zn, Zr and Li to be respectively 0.4634, 0.2891, 0.2475 and >0.0001. The wt % Pd was 0.23%.

EXAMPLE 14 (COMPARATIVE)

Preparation of Catalyst H with a Mn:Zn:Zr Ratio of 0.37:0.38:0.25

In 500 ml of distilled water 43.06 g $Mn(NO_3)_2 \cdot 6H_2O$, 44.55 g $Zn(NO_3)_2 \cdot 6H_2O$ and 34.69 g $ZrO(NO_3)_2 \cdot xH_2O$ were dissolved, making a solution that was 0.90 Molar in transition metals. This solution added over the course of 30 minutes, with constant stirring, to 600 ml of water held at 70° C. The pH of this 600 ml was initially adjusted to pH 9.0 with LiOH. Over the course of the addition, the addition rate of the transition metal solution and of 42.0 g $LiOH \bullet H_2O$/ liter was controlled to maintain a pH of 9.0. Stirring was continued for five hours at 70° C. The suspension was allowed to cool and settle overnight. The precipitate was isolated by filtration. The filtrate had a pH of 9.43. The solids were resuspended in one liter of distilled water and stirred vigorously for 30 minutes, then recovered by filtration. The pH of the filtrate was 8.98. This washing step was repeated twice. The pH of the second filtrate was 8.61 and that of the final filtrate was 7.72. The solids were dried overnight at 130° C. 35.63 g of dried, brownish black solid were recovered. This material was ground to a fine powder. A portion of this material was calcined in air in a tube furnace, the temperature of which was raised from room temperature to 425° C. over the course of two hours, held at 425° C. for two hours and allowed to cool to room temperature over the course of two hours. 20.16 g of cooled calcined solids were treated with 10 ml of distilled water in which 0.1263 g of $Pd(NO_3)_2$ was dissolved along with 20 drops of ethanolamine. After through mixing, the slurry was dried in a vacuum oven for six hours. After drying, the Pd-loaded solids were calcined in air, the temperature of which was raised from room temperature to 425° C. over the course of two hours, held at 425° C. for two hours and allowed to cool to room temperature over the course of two hours. The resulting material had a bulk atomic ratio of Mn to Zn to Zr to Li of 0.3675, 0.381, 0.2491 and 0.001476 respectively.

EXAMPLE 15 (COMPARATIVE)

Preparation of Catalyst I with an Mn:Zn:Zr:Li Ratio of 0.25:0.00:0.65:0.10

In 500 ml of distilled water 41.0 g of 50% $Mn(NO_3)_2 \cdot 6H_2O$ solution and 58.0 g $ZrO(NO_3)_2 \cdot xH_2O$ were dissolved. This solution was added at the rate of 200 drops/minute to 1000 mls of distilled water, the pH of which had previously been adjusted to 9.0 through the drop-wise addition of 2.0 Molar LiOH solution. The pH of the mixture was maintained at 9.0 through the continuous addition of 2.0 Molar LiOH solution. The mixture temperature was maintained at about 70° C. throughout the addition. The slurry containing the precipitate was aged overnight at 70° C. The solids were then recovered by filtration and the filtrate had a pH of 6.98. The solids were resuspended in one liter of distilled water and stirred vigorously for 30 minutes before filtering. The filtrate had a pH of 6.36. The washing step was repeated and the final filtrate had a pH of 6.01. The gelatinous brownish maroon solid was dried overnight at 130° C. 19.25 g of solids were recovered. These were finely ground and calcined at 425° C. as in example above. 5 g of this solid were loaded with Pd as above. The Pd-loaded and dried catalyst was heated in air with the temperature increased from ambient to 325° C. over the course of one hour. The temperature was held at 325° C. for three hours, then cooled over the course of one hour.

This material had a surface area of about 206 $m^2/g$, and the ratio of mole fraction of Mn, Zr and Li respectively was 0.2467, 0.6487 and 0.1041. The Pd loading was 0.23 wt %.

EXAMPLE 16 (COMPARATIVE)

Preparation of Catalyst J with a Mn:Zn:Zr:Li Ratio of 0.33:0.00:0.63:0.04

In 500 ml of distilled water 41.1 g $Mn(NO_3)_2 \cdot 6H_2O$, and 115.6 g $ZrO(NO_3)_2 \cdot xH_2O$ were dissolved and added drop-wise to 500 ml of water adjusted to pH 9.0 with LiOH. 42.0 g of $LiOH \bullet H_2O$ dissolved in 1000 ml of water was simultaneously added drop-wise (at about 1 drop per second) to the initial 500 ml so as to attempt to maintain a constant pH of 9.0. The temperature of the slurry was between about 60° C. and about 65° C. during the precipitation. The pinkish brown slurry was stirred overnight at 65° C. The recovered precipitate was washed three times with two liters of distilled water and air dried for about 60 hours before calcining.

20 g of the solid were loaded with Pd as follows: 0.1240 g of $Pd(NO_3)_2 \cdot 2H_2O$ were dissolved in 20 ml of water along with 24 to 30 drops of ethanolamine. This was thoroughly mixed with 20.0 g of the calcined mixed oxide and dried in a 130° C. vacuum oven for three hours prior to calcination. The Pd-loaded and dried catalyst was heated in air with the temperature increased from ambient to 325° C. over the course of one hour. The temperature was held at 325° C. for three hours, then cooled over the course of one hour.

This material had a surface area of about 92 $m^2/g$, and the ratio of mole fraction of Mn, Zr and Li respectively was 0.3293, 0.6288 and 0.0418. The Pd loading was 0.24 wt %.

EXAMPLE 17 (COMPARATIVE)

Preparation of Catalyst K, $ZnMn_2O_4$ Phase, Mn:Zn:Zr Ratio of 0.68:0.32

In 500 ml of distilled water 57.41 g $Mn(NO_3)_2 \cdot 6H_2O$ and 29.70 g $Zn(NO_3)_2 \cdot 6H_2O$ were dissolved, making a solution that was 0.6 Molar in transition metals with a pH of 2.32. This solution was added over the course of 30 minutes, with constant stirring, to 600 ml of water held at 70° C. along with a 2.0 Molar LiOH solution. The pH of this 600 ml was initially adjusted to pH 9.0 with LiOH. Over the course of the addition, the addition rate of the transition metal solution and of 2.0 Molar LiOH was controlled to maintain a pH of 9.0. Stirring was continued for five hours at 70° C., then left unstirred to cool overnight. A creamy white gel resulted. The precipitate was isolated by filtration. The filtrate had a pH of 7.27. On resuspension the solid darkened to orange brown. The filtrate from this washing had a pH of 7.79. After the second washing, the recovered air-dried orange brown powder was calcined directly, the temperature of which was raised from room temperature to 425° C. over the course of two hours, held at 425° C. for two hours and allowed to cool to room temperature over the course of two hours. 13.79 g of dry material were recovered. 14.81 g of this material were treated with 10 ml of distilled water in which 0.0927 g of $Pd(NO_3)_2$ was dissolved along with 15 drops of ethanolamine. After thorough mixing, the slurry was dried in a vacuum oven for 1.25 hours, then calcined in air. Over the course of an hour, the temperature was increased from room temperature to 325° C., then held at 325° C. for three hours before cooling to room temperature over the course of two hours.

The BET surface area was 35.7 $m^2/g$, and elemental analysis showed mole fractions of the Mn, Zn and Li to be respectively 0.6766, 0.3230 and 0.0001. The wt % Pd was 0.21%.

turned brown as addition continued. The suspension was stirred for six hours at 70° C. The suspension was allowed to settle for about 60 hours at room temperature without stirring. The precipitate was isolated by filtration, then washed three times by resuspension and stirring in a liter of distilled water for an hour at room temperature, followed by filtering to recover the solids for further resuspension. The washed solids were dried at 130° C. for about 64 hours. The dried brownish-black material was ground to a fine powder and calcined in air in a tube furnace, the temperature of which was raised from room temperature to 425° C. over the course of two hours, held at 425° C. for two hours, and allowed to cool to room temperature over the course of two hours. 15.00 g of dry material were recovered. 15.0 g of this material, ground to a fine powder, were treated with 15 ml of distilled water in which 0.0930 g of $Pd(NO_3)_2 \cdot xH_2O$ (assay 39.95 wt % Pd) was dissolved along with 15 to 20 drops of ethanolamine. It was then calcined by heating over the course of one hour to 325° C., held at 325° C. for three hours, and then cooled to room temperature over the course of one hour. After thorough mixing, the slurry was dried in a vacuum oven at 80° C. overnight.

Table 1 shows the composition and surface area of the catalysts. Composition is by relative atomic fraction of the metallic elements in the mixed metal oxide phase(s) of the catalyst analyzed in the protocatalyst. "MMF" means metal mold fraction. Preferred versions of the catalyst are designated A, B, and C.

TABLE 1

| | Catalyst Composition | | | | | | Surface Area |
|---|---|---|---|---|---|---|---|
| | Mn MMF | Zn MMF | Zr MMF | Li MMF | Zr/ (Mn + Zr) | Zn/ (Mn + Zr) | BET $m^2/g$ |
| A | 0.3841 | 0.2592 | 0.2954 | 0.061255 | 0.4347 | 0.3815 | 74.1 |
| B | 0.3857 | 0.2706 | 0.3428 | 0.000963 | 0.4706 | 0.3714 | 75.1 |
| C | 0.4202 | 0.2914 | 0.2884 | — | 0.4288 | 0.3838 | 72.1 |
| D | 0.4023 | 0.2823 | 0.3154 | — | 0.4395 | 0.3933 | 78.8 |
| E | 0.5390 | 0.2892 | 0.1674 | 0.004428 | 0.2370 | 0.4094 | 59.0 |
| F | 0.2663 | 0.2184 | 0.5116 | 0.003681 | 0.6577 | 0.2808 | 112.2 |
| G | 0.4634 | 0.2891 | 0.2475 | — | 0.3482 | 0.4067 | 100.0 |
| H | 0.3675 | 0.3819 | 0.2491 | 0.001476 | 0.4040 | 0.6194 | — |
| I | 0.2467 | 0.0000 | 0.6487 | 0.104117 | 0.7253 | 0.0000 | 206.2 |
| J | 0.3293 | 0.0000 | 0.6288 | 0.041848 | 0.6563 | 0.0000 | 91.9 |
| K | 0.6766 | 0.3230 | 0.0000 | 0.0001 | 0.0000 | 0.4773 | 35.7 |
| L | 0.4165 | 0.2925 | 0.2910 | — | 0.5000 | 0.5000 | 67.9 |

EXAMPLE 18 (COMPARATIVE)

Preparation of Protocatalyst L at pH 11 with Mn:Zn:Zr Ratio of 0.42:0.29:0.29

In 500 ml of distilled water 21.53 g $Mn(NO_3)_2 \cdot 6H_2O$, 14.85 g $Zn(NO_3)_2 \cdot 6H_2O$ and 23.12 g $ZrO(NO_3)_2 \cdot xH_2O$ were dissolved. This solution was added over the course of 30 minutes, with constant stirring, to 600 ml of water held at 70° C. The pH of this 600 ml was initially adjusted to pH 11.0 with LiOH. Over the course of the addition, the addition rate of the transition metal solution and of a 21.0 g/500 ml solution of $LiOH \cdot H_2O$ (F.W. 41.96) was controlled to maintain a pH of 11.0. On addition of the transition metal solution and lithium hydroxide, the precipitate slurry was very light, almost white at the outset. The color slowly

EXAMPLE 19

Table 2 is a comparison of the performance of catalysts within the scope of the invention with catalysts with compositions outside the scope of the present invention. Reaction conditions were 3.00 $cm^3$ of 60 to 80 mesh catalyst volume in the copper-lined reactor tube, about 6500 kPa, 44% CO, 39.4% $H_2$, 6.6% $CO_2$ and 10.0% Ar synthesis gas, into which was vaporized at a rate of 0.8 liquid hourly space velocity a mixture of 90.00 wt % methanol, 9.56 wt % ethanol and 0.44% water. Contact time is in seconds. Temperature is in °C. iBuOH=isobutanol, MBuOH=methyl butanols, nPrOH=n-propanol, EtOH=ethanol. Others=other liquid products, including: n-butanol, n-pentanol, methyl pentanols, etc. CNV=ethanol conversion.

TABLE 2

| Catalyst Mn:Zn:Zr Atomic Fractions | Reactor Temp. | Contact Time | CNV % | C₂+ Liquid Product Composition, Weight % | | | | |
|---|---|---|---|---|---|---|---|---|
| | | | | iBuOH | MBuOH | nPrOH | EtOH | Others |
| A | 380 | 9.5 | 99.5 | 75 | 4 | 10 | 0.3 | 11 |
| 0.384:0.259:0.295 | 360 | 13.6 | 98.0 | 76 | 7 | 8 | 0.7 | 9 |
| 2M LiOH, 70° C. ppt | 340 | 13.3 | 94.6 | 75 | 8 | 5 | 4 | 8 |
| | 320 | 13.2 | 61.9 | 36 | 5 | 20 | 30 | 9 |
| C | 380 | 12.6 | 99.5 | 72 | 7 | 6 | 0.4 | 15 |
| 0.420:0.291:0.288 | 340 | 13.5 | 91.5 | 66 | 12 | 11 | 6 | 5 |
| 1M LiOH 70° C. ppt | | | | | | | | |
| D | 380 | 12.6 | 99.4 | 72 | 7 | 8 | 0.4 | 13 |
| 0.402:0.282:0.315 | 340 | 13.5 | 86.4 | 59 | 10 | 14 | 10 | 7 |
| 1M LiOH 25° C. ppt | | | | | | | | |
| E | 380 | 14.4 | 98.8 | 81 | 5 | 2 | 0.8 | 10 |
| 0.384:0.286:0.164 | 360 | 13.1 | 83.6 | 67 | 7 | 7 | 12 | 8 |
| 1M LiOH 70° C. ppt | 340 | 13.5 | 81.8 | 56 | 7 | 16 | 13 | 7 |

EXAMPLE 20

Table 3 is a further comparison of preferred catalysts to other Pd-loaded Mn:Zn:Zr mixed oxide catalysts. Reaction conditions were 3.00 cm³ of 60 to 80 mesh catalyst volume in the copper-lined reactor tube, about 6500 kPa, 44% CO, 39.4% $H_2$, 6.6% $CO_2$ and 10.0% Ar synthesis gas, into which was vaporized at a rate of 0.8 liquid hourly space velocity a mixture of 90.00 wt % methanol, 9.56 wt % ethanol and 0.44% water. Temperature is in °C. iBuOH= isobutanol, MBuOH=methyl butanols, nPrOH=n-propanol, EtOH=ethanol. Others=other liquid products, including: n-butanol, n-pentanol, methyl pentanols etc. CNV=ethanol conversion.

EXAMPLE 21

Table 4 is a comparison of Mn:Zn:Zr catalysts to catalysts lacking either Zn or Zr. Reaction conditions were 3.00 cm³ of 60 to 80 mesh catalyst volume in the copper-lined reactor tube, about 6500 kPa, 44% CO, 39.4% $H_2$, 6.6% $CO_2$ and 10.0% Ar synthesis gas, into which is vaporized at a rate of 0.8 liquid hourly space velocity a mixture of 90.00 wt % methanol, 9.56 wt % ethanol and 0.44% water. Contact time is in seconds. Temperature is in °C. iBuOH=isobutanol, MBuOH=methyl butanols, nPrOH=n-propanol, EtOH= ethanol. Others=other liquid products, including: n-butanol, n-pentanol, methyl pentanols etc. CNV=ethanol conversion.

TABLE 3

| Catalyst | T ° C. | CNV | C₂+ Liquid Product Composition, Weight % | | | | |
|---|---|---|---|---|---|---|---|
| | | | iBuOH | MBuOH | nPrOH | EtOH | Others |
| A | 380 | 99.5 | 75 | 4 | 10 | 0.3 | 11 |
| 0.384:0.259:0.295 | 360 | 98.0 | 76 | 7 | 8 | 0.7 | 9 |
| 2M LiOH, 70° C. ppt | 340 | 94.6 | 75 | 8 | 5 | 4 | 8 |
| | 320 | 61.9 | 36 | 5 | 20 | 30 | 9 |
| C | 380 | 99.5 | 72 | 7 | 6 | 0.4 | 15 |
| 0.420:0.291:0.288 | 340 | 91.5 | 66 | 12 | 11 | 6 | 5 |
| 1M LiOH 25° C. ppt | | | | | | | |
| D | 380 | 99.4 | 72 | 7 | 8 | 0.4 | 13 |
| 0.402:0.282:0.315 | 340 | 86.4 | 59 | 10 | 14 | 10 | 7 |
| 1M LiOH 70° C. ppt | | | | | | | |
| E | 380 | 98.8 | 81 | 5 | 2 | 0.8 | 10 |
| 0.384:0.286:0.164 | 360 | 83.6 | 67 | 7 | 7 | 12 | 8 |
| 1M LiOH 70° C. ppt | | | | | | | |
| F | 380 | 99.6 | 74 | 7 | 5 | <1 | 13 |
| 0.266:0.218:0.512 | 340 | 77.7 | 48 | 8 | 16 | 17 | 11 |
| G | 380 | 99.5 | 70 | 7 | 7 | <1 | 15 |
| 0.463:0.289:0.247 | 350 | 72.0 | 41 | 9 | 19 | 22 | 8 |
| H | 380 | 95.7 | 72 | 6 | 7 | <1 | 14 |
| 0.367:0.382:0.249 | 340 | 82.6 | 48 | 9 | 16 | 16 | 11 |

TABLE 4

| Catalyst | T °C. | CNV | C$_2$+ Liquid Product Composition, Weight % | | | | |
|---|---|---|---|---|---|---|---|
| | | | iBuOH | MBuOH | nPrOH | EtOH | Others |
| A | 380 | 99.5 | 75 | 4 | 10 | 0.3 | 11 |
| 0.384:0.259:0.295 | 360 | 98.0 | 76 | 7 | 8 | 0.7 | 9 |
| 2M LiOH, 70° C. ppt | 340 | 94.6 | 75 | 8 | 5 | 4 | 8 |
| | 320 | 61.9 | 36 | 5 | 20 | 30 | 9 |
| I | 380 | 99.5 | 72 | 5 | 9 | 0.3 | 13 |
| 0.247:0.000:0.649 | 360 | 94.5 | 73 | 6 | 6 | 4 | 1 |
| | 340 | 59.8 | 36 | 6 | 21 | 32 | 4 |
| J 0.25% Pd | 380 | 97.4 | 74 | 6 | 6 | 2 | 12 |
| 0.329:0.629 | 360 | 86.0 | 63 | 6 | 11 | 10 | 9 |
| | 340 | 56.6 | 36 | 5 | 17 | 35 | 6 |
| K ZnMn$_2$O$_4$ | 380 | 93.9 | 72 | 7 | 9 | 4 | 7 |
| 0.677:0.323:0.000 | 340 | 28.7 | 17 | 0 | 20 | 63 | 0 |

EXAMPLE 22

Table 5 is a comparison of the preferred catalysts of this invention, Pd on Mn:Zn:Zr mixed oxide catalysts, to literature catalysts. Reaction conditions were 3.00 cm$^3$ of 60 to 80 mesh catalyst volume in the copper-lined reactor tube, about 6500 kPa, 44% CO, 39.4% H$_2$, 6.6% CO$_2$ and 10.0% Ar synthesis gas, into which was vaporized at a rate of 0.8 liquid hourly space velocity a mixture of 90.00 wt % methanol, 9.56 wt % ethanol and 0.44% water. Temperature is in °C. iBuOH=isobutanol, MBuOH=methyl butanols, nPrOH=n-propanol, EtOH=ethanol. Others=other liquid products, including: n-butanol, n-pentanol, methyl pentanols etc. CNV=ethanol conversion.

EXAMPLE 23

Table 6 shows the impact of time under synthesis gas at about 380° C. on the conversion of a protocatalyst into a catalyst. Reaction conditions: 3.00 cm$^3$ of 60 to 80 mesh catalyst volume in the copper-lined reactor tube, about 6500 kPa, 44% CO, 39.4% H$_2$, 6.6% CO$_2$ and 10.0% Ar synthesis gas, into which is vaporized at a rate of 0.8 liquid hourly space velocity a mixture of 90.00 wt % methanol, 9.56 wt % ethanol and 0.44% water. Temperature is in °C. Hours is hours at 380° C. under synthesis gas. iBuOH=isobutanol, MBuOH=methyl butanols, nPrOH=n-propanol, EtOH=ethanol. Others=other liquid products, including: n-butanol, n-pentanol, methyl pentanols, etc. CNV=ethanol conversion.

TABLE 5

| Catalyst MMF; Mn:Zn:Zr | T °C. | Hrs on Line | CNV | C$_2$+ Liquid Product Composition, Weight % | | | | |
|---|---|---|---|---|---|---|---|---|
| | | | | iBuOH | MBuOH | nPrOH | EtOH | Others |
| A | 380 | 87 | 99.5 | 75 | 4 | 10 | 0.3 | 11 |
| 0.384:0.259:0.295 | 360 | 111 | 98.0 | 76 | 7 | 8 | 0.7 | 9 |
| 2M LiOH, 70° C. ppt | 340 | 120 | 94.6 | 75 | 8 | 5 | 4 | 8 |
| | 320 | 135 | 61.9 | 36 | 5 | 20 | 30 | 9 |
| CeC$_2$ Alfa | 380 | 119 | 82.1 | 56 | 4 | 21 | 12 | 7 |
| | 360 | 143 | 32.6 | 16 | 3 | 19 | 59 | 3 |
| MgO | 380 | 2 | 88.1 | 70 | 2 | 18 | 8 | 1 |
| | 380 | 28 | 65.4 | 40 | 2 | 30 | 27 | 12 |

TABLE 6

| Catalyst MMF; Mn:Zn:Zr | T °C. | Hrs | CNV | C2$^+$ Liquid Product Composition, Weight % | | | | |
|---|---|---|---|---|---|---|---|---|
| | | | | iBuOH | MBuOH | nPrOH | EtOH | Others |
| A | 380 | 87 | 99.5 | 75 | 4 | 10 | 0.3 | 11 |
| 0.384:0.259:0.295 | 360 | 111 | 98.0 | 76 | 7 | 8 | 0.7 | 9 |
| 2M LiOH, 70° C. ppt | 340 | 120 | 94.6 | 75 | 8 | 5 | 4 | 8 |
| | 320 | 135 | 61.9 | 36 | 5 | 20 | 30 | 9 |
| C | 380 | 89 | 99.5 | 72 | 7 | 6 | 0.4 | 15 |
| 0.420:0.291:0.288 | 340 | 112 | 91.5 | 66 | 12 | 11 | 6 | 5 |
| 1M LiOH, 70° C. ppt | | | | | | | | |

TABLE 6-continued

| Catalyst | | | | C2+ Liquid Product Composition, Weight % | | | | |
|---|---|---|---|---|---|---|---|---|
| MMF; Mn:Zn:Zr | T ° C. | Hrs | CNV | iBuOH | MBuOH | nPrOH | EtOH | Others |
| C<br>0.420:0.291:0.288<br>1M LiOH 70° C. ppt | 340 | 18 | 85.4 | 57 | 9 | 13 | 11 | 10 |

EXAMPLE 24

Table 7 is a comparison of catalysts with preferred bulk compositions prepared from oxide precursors precipitated under various conditions. Reaction conditions were 3.00 cm$^3$ of 60 to 80 mesh catalyst volume in the copper-lined reactor tube, about 6500 kPa, 44% CO, 39.4% H$_2$, 6.6% CO$_2$ and 10.0% Ar synthesis gas, into which is vaporized at a rate of 0.8 liquid hourly space velocity a mixture of 90.00 wt % methanol, 9.56 wt % ethanol and 0.44% water. Temperature is in °C. iBuOH=isobutanol, MmuOH =methyl butanols, nPrOH=n-propanol, EtOH=ethanol. Others=other liquid products, including: n-butanol, n-pentanol, methyl pentanols, etc. CNV=ethanol conversion.

TABLE 7

| Catalyst | | | C$_2$+ Liquid Product Composition, Weight % | | | | |
|---|---|---|---|---|---|---|---|
| MMF; Mn:Zn:Zr | T ° C. | CNV | iBuOH | MBuOH | nPrOH | EtOH | Others |
| A | 380 | 99.5 | 75 | 4 | 10 | 0.3 | 11 |
| 0.384:0.259:0.295 | 360 | 98.0 | 76 | 7 | 8 | 0.7 | 9 |
| 2M LiOH, 70° ppt | 340 | 94.6 | 75 | 8 | 5 | 4 | 8 |
| | 320 | 61.9 | 36 | 5 | 20 | 30 | 9 |
| C | 380 | 99.4 | 72 | 7 | 8 | 0.4 | 13 |
| 0.420:0.294:0.288 | 340 | 86.4 | 59 | 10 | 14 | 10 | 7 |
| 1M LiOH 25° C. ppt | | | | | | | |
| D | 380 | 99.5 | 72 | 7 | 6 | 0.4 | 15 |
| 0.402:0.282:0.315 | 340 | 91.5 | 66 | 12 | 11 | 6 | 5 |
| 1M LiOH 70° C. ppt | | | | | | | |
| L | 380 | 99.4 | 73 | 7 | 7 | 0.4 | 12 |
| 0.417:0.292:0.291 | 340 | 75.1 | 44 | 8 | 19 | 19 | 10 |
| pH 11.0 w LiOH 70° C. ppt | | | | | | | |

What is claimed is:

1. A method of making an alkali-doped noble metal loaded mixed manganese, zinc and zirconium oxide isobutanol synthesis proto catalyst, comprising:
   (a) coprecipitating a manganese-, zinc- and zirconium-containing material at essentially constant pH in a range of from 8 to 12 from a solution containing manganese, zinc and zirconium with alkali hydroxides to make the corresponding oxyhydroxide;
   (b) washing the precipitate to remove soluble alkali salts;
   (c) calcining the precipitate from step (b) in an oxygen containing gas at between about 360° C. and about 430° C. to form a mixed metal oxide of the precipitate;
   (d) loading the mixed metal oxide of step (c) with a noble metal or a mixture of noble metals;
   (e) drying the noble-metal-loaded mixed metal oxide of step (d);
   (f) reducing the material of step (e) in a hydrogen-containing gas to produce a highly dispersed noble metal protocatalyst.

2. The method of claim 1, wherein the pH is in a range of from about 8.5 to about 10.

3. The method of claim 1, wherein the alkali hydroxide is selected from the group consisting of LiOH, NaOH, KOH, RbOH, CsOH and mixtures thereof.

4. The method of claim 1, wherein the noble metal dispersion is from about 75% to about 100%.

5. The method of claim 1, further comprising drying the precipitate of step (b).

6. The method of claim 1, wherein the noble metal solution contains from about 9 to about 36 moles of ethanolamine per mole of noble metal.

7. The method of claim 1 wherein the noble metal is selected from the group consisting of platinum and palladium.

8. A proto catalyst for conversion of methanol, ethanol and mixtures thereof with n-propanol to isobutanol, made by the method of:
   (a) coprecipitating a manganese-, zinc- and zirconium-containing material at essentially constant pH in a range of from 8 to 12 from a solution containing manganese, zinc and zirconium with alkali hydroxides to make the corresponding oxyhydroxide;
   (b) washing the precipitate to remove soluble alkali salts;
   (c) calcining the precipitate from step (b) in an oxygen containing gas at between about 360° C. and about 430° C. to form a mixed metal oxide of the precipitate;
   (d) loading the mixed metal oxide of step (c) with a noble metal or a mixture of noble metals;
   (e) drying the noble-metal-loaded mixed metal oxide of step (d);
   (f) reducing the material of step (e) in a hydrogen-containing gas to produce a highly dispersed noble metal protocatalyst.

9. The catalyst of claim 8 wherein the pH is in a range of from about 8.5 to about 10.

* * * * *